United States Patent
Vahey et al.

(10) Patent No.: US 7,495,221 B2
(45) Date of Patent: Feb. 24, 2009

(54) METHOD AND SYSTEM FOR MEASURING OPTICAL PROPERTIES OF SCATTERING AND ABSORBING MATERIALS

(75) Inventors: David W. Vahey, Madison, WI (US); Jun Yong Zhu, Madison, WI (US); Carl J. Houtman, Madison, WI (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 16 days.

(21) Appl. No.: 11/803,484

(22) Filed: May 15, 2007

(65) Prior Publication Data

US 2008/0283757 A1    Nov. 20, 2008

(51) Int. Cl.
G01N 21/17 (2006.01)
(52) U.S. Cl. .................................. 250/341.1
(58) Field of Classification Search ............. 250/341.1, 250/341.8
See application file for complete search history.

(56) References Cited

U.S. PATENT DOCUMENTS 5,912,730 A * 6/1999 Dahm et al. ............... 356/72
5,991,046 A * 11/1999 Shakespeare et al. ....... 356/429
2006/0293599 A1 * 12/2006 Sardar et al. ............... 600/476

OTHER PUBLICATIONS

Vahey et al., "On Measurements of Effective Residual Ink Concentration (ERIC) of Deinked Papers Using Kubelka-Munk Theory." Progress in Paper Recycling, vol. 16, No. 1 (Nov. 2006) pp. 3-12.*
Hebert et al., "Reflectance and transmittance model for recto-verso halftone prints." J. Opt. Soc. Am. A, vol. 23, No. 10 (Oct. 2006) pp. 2415-2432.*

* cited by examiner

*Primary Examiner*—Constantine Hannaher
(74) *Attorney, Agent, or Firm*—John D. Fado; Lesley D. Shaw; Janet I. Stockhausen

(57) ABSTRACT

A system and method for determining a level of effective residual ink concentration (ERIC) in a piece of recycled paper. The piece of paper is illuminated with a beam of radiation and an amount of the beam of radiation reflected and transmitted by the piece of paper is measured. The level of ERIC is determined as a function of the reflected and transmitted radiation.

27 Claims, 2 Drawing Sheets

METHOD AND SYSTEM FOR MEASURING OPTICAL PROPERTIES OF SCATTERING AND ABSORBING MATERIALS

STATEMENT OF GOVERNMENT RIGHTS

This invention was made with United States Government support under contract awarded by the USDA Forest Service. The United States Government has certain rights in the invention.

FIELD OF THE INVENTION

The present invention generally relates to measuring ink concentrations in paper and, in particular, measuring a level of effective residual ink concentration (ERIC) in a piece of recycled paper.

BACKGROUND OF THE INVENTION

Ink removal is one of the most important steps in recycling of mixed office wastepaper, old magazine, and old newsprint. Ink removal efficiency of a recycling operation is characterized by the brightness increment of the final paper over that of feed stock. Final paper brightness has been used as a product specification of recycled papers. However, the brightness measure has deficiencies in quantifying ink-removal efficiency and the amount of residual ink in de-inked pulp because paper brightness depends on additional factors, such as pulp refining, pressing, calendering, and formation. Jordan and Popson developed a radiation reflectance technique to measure residual ink concentration in paper made of de-inked pulp using Kubelka-Munk theory. The technique measures reflectance at an infrared wavelength (~950 nm) from a paper sample over a black backing, R0, and reflectance from a thick stack of paper from the same sample, R∞. The Kubelka-Munk constant k, the specific absorption coefficient of the sample, can be calculated from the two measured reflectance values, R0 and R∞. It is directly related to the residual ink concentration in the paper sample when measured at a near infrared wavelength where the absorption from lignin and dyes can be ignored.

According to this approach, the specific absorption coefficient, k, is $$k = s \frac{(1 - R_\infty)^2}{2 R_\infty}$$

where the specific scatter coefficient, s, is $$s = \left[ \frac{R_\infty}{w(1 - R_\infty^2)} \right] \ln \left[ \frac{1 - R_0 R_\infty}{1 - R_0 / R_\infty} \right]$$

and w is the basis weight.

In particular, the commonly used approach employs a detector measuring the reflected radiation from a test paper. The paper specimen is removed, placed in front of a stack of equivalent papers, and replaced with the stack in the sample holder. At this time, the reflected radiation is measured a second time. The two values of reflected radiation are used to determine ERIC. Problems with this method occur when the samples are so opaque to the radiation that both values are the same, or nearly so. In that case the equation to calculate ERIC leads to inaccurate values. The remount of the test specimen on the stack also induces error in measurement because the specimen cannot be repositioned exactly as it was. The degree of contact between the papers in the stack also changes, introducing further measurement variability.

This accepted method for measuring effective residual ink concentration (ERIC) in recycled papers is limited to papers having opacity values less than 97.0. This is because the method is based on diffuse reflection from papers measured once with a black backing and again with a thick backing of similar papers. The two reflection values become statistically indistinguishable at high opacities. ERIC values are undetermined owing to a logarithmic singularity in the defining equation. Even when ERIC values can be calculated, their uncertainty is amplified by the singularity to the point where predicted coefficients of variation (COV) exceed 50% in papers near the opacity limit. For example, in five repeat tests of a sample containing five similar handsheets, individual ERIC values ranged from 309 to 858 ppm, even though the average opacity for the sample was an acceptable 96.1. The lower end of this range is close to the average ERIC for commercial papers, whereas the upper end is close to three times the commercial average. This renders the test marginally useful as a way to monitor the de-inking process.

SUMMARY OF THE INVENTION

A new approach to measuring ERIC values uses the measurement of diffuse reflection and transmission to single sheets. The Kubelka-Munk theory is again applied to the data, and there is no change in the meaning of ERIC. The measurement is valid at any opacity for which there is quantifiable transmission through the sheet in the near-infrared spectral region. Coefficients of variation (COV) are as low as those from the accepted ERIC measurement throughout the commercial range. They decrease with increasing opacity to a low of 10% measured for a sheet having 98.7 opacity and 1110 ppm ERIC. In contrast with the accepted method, the COV is relatively insensitive to the value of the scattering coefficient of the paper specimen. The system and method of the invention provide a way to monitor de-inking progress in recycled papers.

Other objects and features will be in part apparent and in part pointed out hereinafter.

BRIEF DESCRIPTION OF THE DRAWINGS

FIG. 1A is a diagram illustrating one embodiment of the invention in which a filter is employed for preventing visible radiation from being transmitted to the detectors.

Corresponding reference characters indicate corresponding parts throughout the drawings.

DESCRIPTION OF THE EMBODIMENTS

The present invention is a method and system for measuring the ERIC of a piece of paper, typically a hand sheet 6 inches in diameter with a density of about 50 grams/m² and a total weight of about 1.2 grams. According to one embodiment of the invention, radiation reflected from the first surface and radiation transmitted through the piece of paper are measured to determine the ERIC of the paper. The method and system of the invention is particularly useful for papers having higher ink concentrations and/or higher opacity which papers generally do not reflect a consistently measurable amount of radiation. One reason for this is that reflection essentially requires radiation to pass through at least part of the piece of paper twice. If a stack is present, all of the radiation that passes into the stack must pass again through the piece of paper before detection, thus substantially reducing the amount of reflected radiation for higher opacity paper. On the other hand, transmission only requires radiation to pass through the piece of paper once, thus increasing the amount of transmitted radiation as compared to the amount of reflected radiation.

Figure 1:
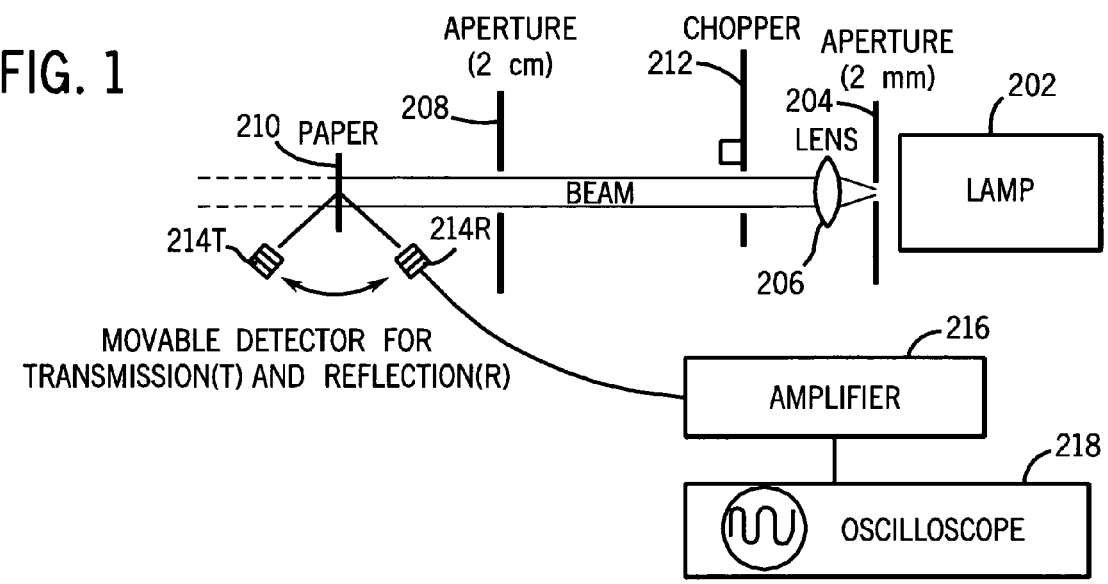
FIG. 1 is a diagram illustrating one embodiment of the invention in which a moveable detector is employed for sensing radiation reflected by the paper sample and for sensing radiation transmitted by the paper sample.

According to one embodiment of the invention as illustrated in FIG. 1, a radiation source such as a tungsten halogen lamp 202 generates electromagnetic radiation within a wavelength band extending beyond the visible to the near infrared. Preferably, the near infrared radiation is within a wavelength band centered at or near 950 nm (to minimize absorption by the paper constituents other than carbon black), although other bands are contemplated. The generated radiation is formed into a beam by any means known in the art. For example, as illustrated in FIG. 1, an aperture 204 (e.g., 2 mm) followed by a collimating lens 206 may be used to form a partially collimated beam of nominally parallel rays incident on the paper 210. Alternatively, or in addition, a second aperture 208 (e.g., 2 cm) may be used to further control the amount of the radiation beam which illuminates a piece of recycled paper 210 of which the ERIC is being measured. Alternatively, or in addition, a chopper 212 may be in line between the lamp 202 and the paper 210 for selectively illuminating the paper 210.

Figure 1A:
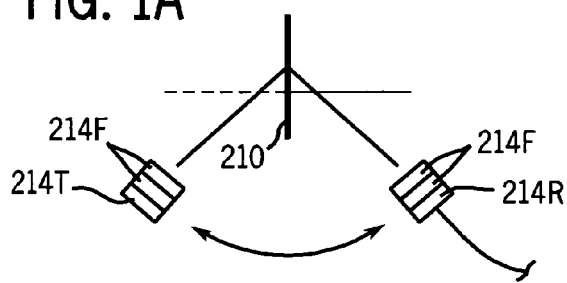
FIG. 1A is a partial exploded view of FIG. 1.

According to one embodiment of the invention as illustrated in FIG 1, part of the radiation beam is reflected by the paper 210 and part of the radiation beam is transmitted through the paper 210. An amount of the radiation beam reflected by the piece of paper 210 is measured, and an amount of the radiation beam transmitted by the piece of paper is measured. Preferably, the measurements are done using radiation detectors 214 sensitive in the near-infrared spectral region near 950 nm, such as Silicon photodiodes. In one embodiment as illustrated in FIG. 1A, spectral filters 214F are inserted in front of the radiation detectors to prevent visible radiation from the source from reaching the detectors. Alternatively, such filters can be placed at any convenient point between the lamp 202 and the piece of paper 210. The level of effective residual ink concentration (ERIC) is then determined as a function of the reflected amount of radiation and as a function of the transmitted amount of radiation.

In one embodiment as illustrated in FIG. 1, a detector 214, such as a photodetector or other sensor sensitive in the near-infrared spectral region is calibrated for detecting radiation reflected and/or transmitted from the paper 210. In one example, a specimen of bleached pulp board may be used for the calibration. The specimen, itself, is preliminarily calibrated against a Magnesium Oxide (MgO) standard used for spectroscopy. A radiation signal detected at position R from the MgO standard is assumed to represent 100% reflectance. A reflected signal from bleached pulp board is measured at position R, and a transmitted signal from the pulp board is measured at position T. A percentage representing the difference between the detected signal for the MgO ant the sum of the detected signals for the pulp board is determined. The amount of the difference is attributed to absorption by the pulp board. An amount of illumination of the paper 210 as signified by the detector (e.g., detector volts) can be subsequently calibrated according to $\lfloor R_{pulpboard}(\text{volts})+T_{pulpboard}(\text{volts})\rfloor/(100\%-\text{Difference Percent})$. Frequent calibrations to determine this value may be performed at the start, the end, and during the sample measurements.

In the embodiment as illustrated in FIG. 1, the detector is a moveable detector 214 that is positioned at position R on one side of the piece of paper 210 and calibrated as discussed above to detect the amount of the incident radiation beam that is reflected by the paper 210. At position R, the photodetector absorbs a portion of the radiation beam reflected by the paper 210 and generates a calibrated reflection signal indicative of the total amount of reflected radiation in the wavelength band of interest. The reflection signal has a parameter, such as voltage, which represents the amount of radiation reflected by the paper 210 which reaches the detector 214 in the wavelength band of interest. Thereafter, the detector is moved and positioned on the other side of the piece of paper 210 at position T to detect the amount of the incident radiation beam that is transmitted through the piece of paper 210. At position T, the photodetector absorbs a portion of the radiation beam transmitted by the paper 210 and generates a transmission signal indicative of the amount of transmitted radiation in the wavelength band of interest. The transmission signal has a parameter, such as voltage, which represents the amount of radiation transmitted through the paper 210 in the wavelength band of interest which reaches the detector 214.

The calibrated reflection signal and the calibrated transmission signal are each amplified by an amplifier 216 and displayed by an oscilloscope 218 so that their parameters (e.g., voltage) may be measured and compared to determine the ERIC of the piece of paper 210. Thereafter, the ERIC may be calculated. In one embodiment, the ERIC is calculated as a function of the amplitude of the transmission signal relative to the amplitude of the reflection signal.

In summary, FIG. 1 illustrates one embodiment of a system of determining a level of effective residual ink concentration (ERIC) in the piece of recycled paper 210. The radiation source in the form of lamp 202 illuminates the piece of paper 210 with the radiation beam and the detector 214 in the form of a photosensor measures the amount of the radiation reflected by the piece of paper 210 in the wavelength band of interest when the photosensor is in the R position. As a result, the photosensor provides a first voltage signal indicative of the reflected amount of radiation in the wavelength band of interest. When the photosensor is in the T position, the photosensor measures the amount of the radiation transmitted by the piece of paper 210 in the wavelength band of interest and provides a second voltage signal indicative of the transmitted amount of radiation in the wavelength band of interest. The amplifier 216 and oscilloscope 218 receive the first and second voltage signals and indicate the level of effective residual ink concentration (ERIC) as a function of the first and second voltage signals.

Figure 2:
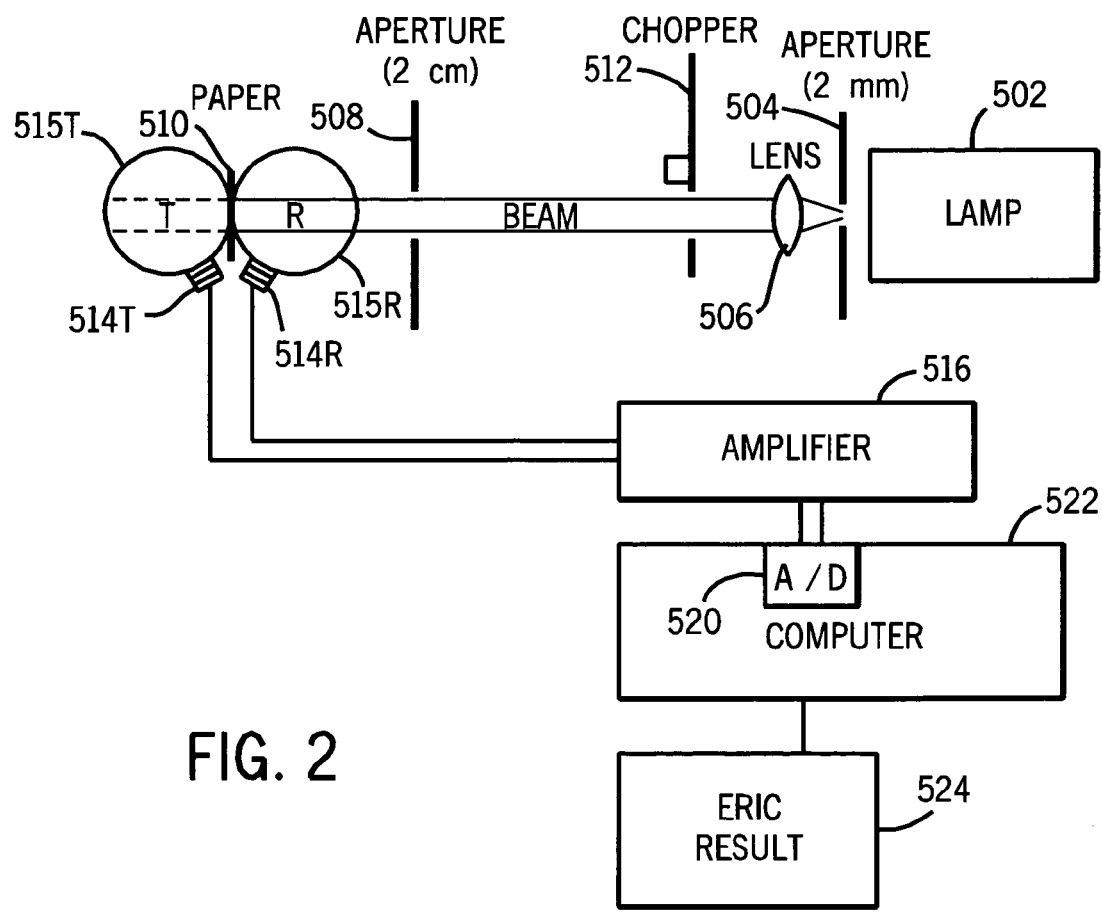
FIG. 2 is a diagram illustrating one embodiment of the invention in which two detectors are employed, one for sensing radiation reflected by the paper sample and another for sensing radiation transmitted by the paper sample.

According to one embodiment of the invention as illustrated in FIG. 2, a radiation source such as a lamp 502 generates radiation within a wavelength band. Preferably, the radiation is within a wavelength band centered about 950 nm, although other bands are contemplated. The generated radiation is formed into a beam by any means known in the art. For example, as illustrated in FIG. 2, an aperture 504 (e.g., 2 mm) followed by a collimating lens 506 may be used to form the beam of partially collimated and/or partially coherent radiation incident on the paper 510. Alternatively, or in addition, a second aperture 508 (e.g., 2 cm) may be used to further control the amount of the radiation beam which illuminates a piece of recycled paper 510 of which the ERIC is being measured. Alternatively, or in addition, a chopper 512 may be in line between the lamp 502 and the paper 510 for selectively illuminating the paper 510.

According to one embodiment of the invention, part of the beam of radiation is reflected by the paper 510 and part of the beam of radiation is transmitted through the paper. An amount of the beam of radiation reflected by the piece of paper 510 is measured, and an amount of the beam of radiation transmitted by the piece of paper is measured. The level of effective residual ink concentration (ERIC) is then determined as a function of the reflected amount of radiation and as a function of the transmitted amount of radiation.

In the embodiment as illustrated in FIG. 2, a first detector 514R, such as a photodetector or other radiation sensor is positioned at a position on one side of the piece of paper 510 adjacent the lamp 502 to detect the amount of the incident radiation beam that is reflected by the paper 510. At this position, the detector 514R absorbs a portion of the radiation beam reflected by the paper 510 and generates a reflection signal indicative of the amount of reflected radiation. The reflection signal has a parameter, such as voltage, which represents the amount of radiation reflected by the paper 510 which reaches the detector 514. A second detector 514T is positioned on the other side of the piece of paper 510 to detect the amount of the incident radiation beam that is transmitted through the piece of paper 510. At this position, the detector 514T absorbs a portion of the radiation beam transmitted by the paper 510 and generates a transmission signal indicative of the amount of transmitted radiation. The transmission signal has a parameter, such as voltage, which represents the amount of radiation transmitted through the paper 501 which reaches the detector 514.

In one embodiment, it is contemplated that a first radiation integrator such as an integrating sphere 515R may be positioned between the piece of recycled paper and the first detector 514R to detect the reflected amount of radiation. Alternatively, or in addition, a second radiation integrator such as an integrating sphere 515T may be positioned between the piece of recycled paper and the second detector 514T to detect the transmitted amount of radiation. For example, the sphere may be a hollow white sphere of non-absorbing, scattering material positioned adjacent the paper and having a detector positioned within the sphere in such a way as to capture nearly all of the transmitted radiation before it can be absorbed or escape the sphere.

The reflection signal and the transmission signal are each amplified by an amplifier 516 so that their parameters (e.g., voltage) may be measured and compared to determine the ERIC of the piece of paper 510. In the embodiment illustrated in FIG. 2, the amplified signals are provided to an analog-to-digital converter 520 which may be a separate component or part of a computer 522 which receives the converted digital signals to calculate the ERIC 524 of the paper 510.

In one embodiment, the computer 522 calculates ERIC according to the following:

ERIC=$(k/k_{ink})*10^6$ (ppm)

In the above equation, k is the specific absorption coefficient of the piece of recycled paper being tested, and $k_{ink}$ is the specific absorption coefficient of ink, where k is $$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

$R = R(w) = (J(w)/I(w))$, and $T = T(0) = (I(0)/I(w))$.

In one embodiment, $k_{ink}$ is a predefined value (e.g., 10,000 m2/kg). As noted in the above equations, w is the grammage of the paper being tested. I(w) is a light flux of the incident beam on the front surface of the paper being tested, as measured by a photosensor 214R or 514R during calibration of the photosensor. J(w) is a light flux of the reflected beam at the front surface of the paper being tested, as measured by a photosensor 214R or 514R after calibration of the photosensor. I(0) is a light flux of the transmitted beam after passing through the paper being tested, as measured by a photosensor 214T or 514T after calibration of the photosensor. In one embodiment, the computer 522 may additionally or alternatively compute a specific scattering coefficient, s, using the following equation $$s = \frac{2R}{w \cdot \sqrt{(1-T^2+R^2)^2 - 4R^2}} \sinh^{-1}\left[\frac{1}{2T}\sqrt{(1-T^2+R^2)^2 - 4R^2}\right].$$

Thus, the present invention measures reflectance R at the incident surface and transmission T at the back surface of a sample and determines the coefficients k and s for determining an optical property of the sample. For a sample with incident light flux I(w) and reflected light flux J(w) at the light-incident surface(x=w, measured in basis weight), differential Kubelka-Munk equations within the sample can be written as $$\frac{dI}{dx} = s\left(\frac{k}{s}+1\right)I - sJ; \text{ and } \frac{dJ}{dx} = sI - s\left(\frac{k}{s}+1\right)J$$

For the case where there is no radiation returned to the sample by reflection at the back surface, i.e., J(0)=0, the solution for the light reflected from the incident surface is $$R = R(w) = \frac{J(w)}{I(w)} = \frac{e^{sbw} - e^{-sbw}}{(a+b)e^{sbw} - (a-b)e^{-sbw}} = \frac{\sinh(sbw)}{a\sinh(sbw) + b\cosh(sbw)}$$

where a=(k/s+1) and $b^2=a^2-1$.

Transmission at the back surface is $$T = T(0) = \frac{I(0)}{I(w)} = \frac{2b}{(a+b)e^{sbw} - (a-b)e^{-sbw}} = \frac{b}{a\sinh(sbw) + b\cosh(sbw)}$$

From the ratio of these two equations, the definitions of a and b, and the hyperbolic identity relation between the cosh and sinh functions, the inverse equations expressing s and k in terms of R and T are defined, as noted above, as $$s = \frac{2R}{w \cdot \sqrt{(1-T^2+R^2)^2 - 4R^2}} \sinh^{-1}\left[\frac{1}{2T}\sqrt{(1-T^2+R^2)^2 - 4R^2}\right] \text{ and}$$

$$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right].$$

In summary, FIG. 2 illustrates one embodiment of a system of determining a level of effective residual ink concentration (ERIC) in the piece of recycled paper 510. The radiation source in the form of lamp 502 illuminates the piece of paper 510 with the radiation beam and the detectors 514R and 514T in the form of photosensors measure the amount of the radiation beam reflected and transmitted by the piece of paper 510, respectively, in the wavelength band of interest. As a result, the detector 514R provides a first voltage signal indicative of the reflected amount of radiation and the detector 514T provides a second voltage signal indicative of the transmitted amount of radiation. The amplifier 516, a/d converter 520 and computer 522 are one example of a processor receiving the first and second voltage signals and determining the level of effective residual ink concentration (ERIC) 524 as a function of the first and second voltage signals. In one embodiment, the computer 520 may be used to compare an amplitude of the reflected amount of radiation in a wavelength band of interest relative to an amplitude of the transmitted amount of radiation in a wavelength band of interest in order to determine the ERIC 524, according to the calculations as discussed above.

In one embodiment the chopper 212, 512 may be used to control processing of signals by the system. In the embodiment of FIG. 2, the chopper 512 may be controlled by the computer 520. In either of the embodiments of FIGS. 1 and 2, the chopper may be manually or automatically controlled. Initially, to calibrate the system, the chopper is closed to prevent the radiation beam from illuminating the piece of paper. With the chopper closed, ambient reflected radiation and ambient transmitted radiation are detected by the photosensor(s). Thereafter, the chopper is opened to permit the beam of radiation to illuminate the piece of paper. With the chopper open the reflected and transmitted radiation is measured. The ambient measurements are then subtracted from the reflected and transmitted radiation measurements to provide calibrated measurements of the amount of radiation reflected by the piece of paper and the amount of radiation transmitted by the piece of paper. The calibrated measurements are then used to determine ERIC of the paper.

In one embodiment, a filter may be provided over the detector(s) to exclude radiation other than radiation within the wavelength band of interest. For example, if the radiation beam is in a wavelength band centered near 950 nm, a visible radiation-blocking filter may be positioned over the detector(s). Alternatively, or in addition, one or more filters can be placed in the optical path between the lamp and the paper. Alternatively or in addition, mirrors may be used to direct the beam of radiation or to capture the reflected or transmitted radiation.

Most commercial devices for measuring the optical properties of paper do so using a method based on measuring reflectance only as opposed to the method of this invention based on measuring reflectance and transmittance. In reflectance only methods, two reflectance measurements are typically required. The two measurements differ, for example, in the number of stacked sheets exposed to the illumination source. (See page 17 of Appendix.) This method may be less expensive to implement and simpler to design in certain paper applications, such as color measurement adapted to measuring ERIC values. The adapted color measurement does not limit application to 125 ppm or low-opacity, but it works well in these limits. For commercial grade newsprint, the two methods work about the same. In one embodiment, the system and method of the invention is best suited for papers with opacity larger than 95% and ERIC values above 500 ppm. In commercial de-inking operations, it is important to have accurate measurements in this region to better control the process in its initial phases. The system and method of the invention can also be very effective in laboratory experiments, where larger ERIC numbers are frequently encountered. Finally, concentration measurements of substances, such measurements similar to ERIC measurements, are made in other industries, such as the fabric dying (measuring the concentration of dye in a fabric sample) or paint industry (measuring paint concentration in a sample), and the system and method of the invention may be relevant for these.

Having described the invention in detail, it will be apparent that modifications and variations are possible without departing from the scope of the invention defined in the appended claims.

The above non-limiting examples are provided to illustrate the present invention.

Although described in connection with an oscilloscope, processor or computer, embodiments of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well known computing systems, environments, and/or configurations that may be suitable for use with aspects of the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions for calculating ERIC. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense. In view of the above, it will be seen that the several objects of the invention are achieved and other advantageous results attained.

What is claimed is:

1. A method of determining a level of effective residual ink concentration (ERIC) in a piece of recycled paper comprising:
    illuminating the piece of paper with a particular beam of electromagnetic radiation;
    measuring from a first side of the piece of paper an amount R of the particular beam of electromagnetic radiation reflected by the piece of paper;
    measuring from a second side of the piece of paper an amount T of the particular beam of electromagnetic radiation transmitted by the piece of paper; and
    determining the level of effective residual ink concentration (ERIC) as a function of the reflected amount of radiation and as a function of the transmitted amount of radiation.

2. The method of claim 1 wherein the particular beam of radiation is within a wavelength band including 950 nm.

3. The method of claim 1 wherein the piece of recycled paper has an opacity level of at least 97%.

4. The method of claim 1 wherein measuring the reflected amount and measuring the transmitted amount comprises positioning a detector on the first side of the piece of recycled paper to detect the reflected amount and positioning the detector on the second side of the piece of paper to detect the transmitted amount.

5. The method of claim 1 wherein measuring the reflected amount and measuring the transmitted amount comprises positioning a first detector on the first side of the piece of recycled paper to detect the reflected amount of electromagnetic radiation and positioning a second detector on the second side of the piece of paper to detect the transmitted amount of electromagnetic radiation.

6. The method of claim 1 wherein measuring the reflected amount and measuring the transmitted amount comprises positioning a first radiation integrator between the piece of recycled paper and a first detector on the first side of the piece of recycled paper to detect the reflected amount of radiation and positioning a second electromagnetic radiation integrator between the piece of recycled paper and a second detector on the second side of the piece of paper to detect the transmitted amount of electromagnetic radiation.

7. The method of claim 1 further comprising at least one of a chopper, a lens and an aperture between an electromagnetic radiation source and the piece of recycled paper for supplying the particular beam of electromagnetic radiation.

8. The method of claim 1 wherein measuring the reflected amount and measuring the transmitted amount comprises employing a detector to detect the reflected amount of electromagnetic radiation R and the transmitted amount of electromagnetic radiation and further comprises a processor for receiving a reflection signal from the detector, said reflection signal indicative of the amount of reflected electromagnetic radiation R, said processor receiving a transmission signal from the detector, said transmission signal indicative of the amount of transmitted electromagnetic radiation T, said processor calculating the ERIC level as a function of the reflection signal and the transmission signal.

9. The method of claim 8 further comprising an analog to digital converter for converting the reflection signal and the transmission signals into digital signals provided to the processor.

10. The method of claim 1 wherein the particular beam of electromagnetic radiation is at least partially collimated.

11. The method of claim 1 wherein determining a level of effective residual ink concentration (ERIC) in a piece of recycled paper comprises comparing an amplitude of the reflected amount of radiation R compared to an amplitude of the transmitted amount of radiation T.

12. The method of claim 1 wherein the determining comprises calculating ERIC according to the following:

$$ERIC = (k/k_{ink}) * 10^6 \text{ (ppm)}$$

wherein k is the specific absorption coefficient of the piece of paper, and $k_{ink}$ is a pre-defined value representing the absorption coefficient of ink, and wherein $$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

wherein w is the grammage of the piece of paper.

13. A system of determining a level of effective residual ink concentration (ERIC) in a piece of recycled paper comprising:
    an electromagnetic radiation source illuminating the piece of paper with a particular beam of electromagnetic radiation;
    a photosensor measuring from a first side of the piece of paper an amount R of the particular electromagnetic radiation beam reflected by the piece of paper and providing a first signal indicative of the reflected amount of electromagnetic radiation, said photosensor measuring from a second side of the piece of paper an amount T of the particular electromagnetic radiation beam transmitted by the piece of paper and providing a second signal indicative of the transmitted amount of radiation; and
    a processor receiving the first and second signals and determining the level of effective residual ink concentration (ERIC) as a function of the first and second signals.

14. The system of claim 13 wherein the particular beam of electromagnetic radiation provided by the radiation source is within a wavelength band including 950 nm.

15. The system of claim 13 wherein the piece of recycled paper has an opacity level of at least 97%.

16. The system of claim 13 wherein the photosensor comprises a photodetector having a first position for measuring the amount R of the particular beam of electromagnetic radiation reflected by the piece of paper and having a second position for measuring the amount T of the particular beam of electromagnetic radiation transmitted by the piece of paper.

17. The system of claim 13 wherein the photosensor comprises a first detector on the first side of the piece of recycled paper to detect the reflected amount R of electromagnetic radiation and a second detector on the second side of the piece of paper to detect the transmitted amount T of radiation.

18. The system of claim 13 further comprising a first electromagnetic radiation integrator positioned between the piece of recycled paper and a first detector on the first side of the piece of recycled paper to detect the reflected amount R of electromagnetic radiation and a second electromagnetic radiation integrator positioned between the piece of recycled paper and a second detector on the second side of the piece of paper to detect the transmitted amount T of electromagnetic radiation.

19. The system of claim 13 further comprising a chopper between the electromagnetic radiation source and the piece of paper for intermittently interrupting the illumination of the piece of paper with the particular beam of electromagnetic radiation.

20. The system of claim 13 further comprising an analog to digital converter for converting the first and second signals into digital signals provided to the processor.

21. The system of claim 13 wherein the particular beam of electromagnetic radiation provided by the radiation source is at least partially collimated radiation.

22. The system of claim 13 wherein the processor compares an amplitude of the first signal to an amplitude of the second signal.

23. The system of claim 13 wherein the processor calculates ERIC according to the following:

$$ERIC = (k/k_{ink}) * 10^6 \text{ (ppm)}$$

wherein k is the specific absorption coefficient of the piece of paper, and $k_{ink}$ is a pre-defined value representing the absorption coefficient of ink, and wherein $$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

wherein w is the grammage of the piece of paper.

24. A system of determining a specific absorption coefficient k of a sample comprising:
an electromagnetic radiation source illuminating the sample with a particular beam of electromagnetic radiation;
a photosensor measuring an amount R of the particular electromagnetic radiation beam reflected by the sample and providing a first signal indicative of the reflected amount R of electromagnetic radiation, said photosensor measuring an amount T of the particular electromagnetic radiation beam transmitted by the sample and providing a second signal indicative of the transmitted amount T of radiation; and
a processor receiving the first and second signals and determining the specific absorption coefficient k of the sample as a function of the first and second signals according to the following:

$$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

wherein w is the grammage of the sample.

25. The system of claim 24 wherein the sample is recycled paper and the specific absorption coefficient k indicates a level of effective residual ink concentration (ERIC) in the recycled paper.

26. A method of determining a specific absorption coefficient k of a sample comprising:
illuminating the sample with a particular beam of electromagnetic radiation;
measuring an amount R of the particular beam of electromagnetic radiation reflected by the sample;
measuring an amount T of the particular beam of electromagnetic radiation transmitted by the sample; and
determining the specific absorption coefficient k of the sample as a function of the reflected amount R of radiation and as a function of the transmitted amount T of radiation according to the following:

$$k = \frac{(1-R)^2 - T^2}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

wherein w is the grammage of the sample.

27. A method of determining a specific scattering coefficient s of a sample comprising:
illuminating the sample with a particular beam of electromagnetic radiation;
measuring an amount R of the particular beam of electromagnetic radiation reflected by the sample;
measuring an amount T of the particular beam of electromagnetic radiation transmitted by the sample; and
determining the specific scattering coefficient s of the sample as a function of the reflected amount R of radiation and as a function of the transmitted amount T of radiation according to the following:

$$s = \frac{2R}{w \cdot \sqrt{(1-T^2+R^2)^2 - 4R^2}} \sinh^{-1}\left[\frac{1}{2T}\sqrt{(1-T^2+R^2)^2 - 4R^2}\right]$$

wherein w is the grammage of the sample.

* * * * *